United States Patent [19]

Yanaihara et al.

[11] Patent Number: 4,517,180

[45] Date of Patent: May 14, 1985

[54] PEPTIDES, PROCESS FOR PREPARING THE SAME AND PSYCHODEPRESSANT COMPOSITIONS CONTAINING THE SAME

[75] Inventors: Noboru Yanaihara, Shizuoka; Nobuo Sugiura, Hashima; Takashi Hiyama, Tokushima, all of Japan

[73] Assignees: Amano Pharmaceutical Co., Ltd, Aichi; Otsuka Pharmaceutical Co., Ltd., Tokyo, both of Japan

[21] Appl. No.: 545,994

[22] Filed: Oct. 27, 1983

[30] Foreign Application Priority Data

Oct. 27, 1982 [JP] Japan .................................. 57-189740
Jul. 20, 1983 [JP] Japan .................................. 58-133065

[51] Int. Cl.$^3$ ...................... A61K 37/00; C07C 103/52
[52] U.S. Cl. .................................. 514/16; 260/112.5 R
[58] Field of Search .................. 260/112.5 R; 424/177

[56] References Cited

U.S. PATENT DOCUMENTS 3,892,726  7/1975  Ondetti et al. .................... 260/112.5

FOREIGN PATENT DOCUMENTS 65222  4/1983  Japan .
28868  6/1983  Japan .
1173539 12/1969 United Kingdom .

OTHER PUBLICATIONS

J. Pluscec et al., J. Med. Chem. 13, 349, (1970).
M. Bodanszky et al., J. Med. Chem. 23, 82, (1980).
J. Martinez et al., J. Med. Chem. 25, 589, (1982).
L. Moroder et al., Hoppe-Seyler's Z. Physiol. Chem. 360, 787, (1979).

Primary Examiner—Delbert R. Phillips
Attorney, Agent, or Firm—Armstrong, Nikaido, Marmelstein & Kubovcik

[57] ABSTRACT

This invention provides a peptide represented by the formula

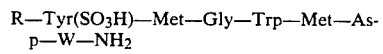

wherein R is HOOC—A—CO—Asp— (wherein A is lower alkylene), pGlu—Asp—, HOOC—A—CO— (wherein A is lower alkylene) or

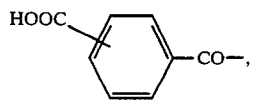

and W is Phe or N$^\alpha$-lower alkyl-Phe, or a salt thereof, process for preparing the peptide and psychodepressant composition containing the peptide.

The peptides of the invention are useful as psychodepressant drug, and especially effective for curing schizophrenia.

12 Claims, No Drawings

PEPTIDES, PROCESS FOR PREPARING THE SAME AND PSYCHODEPRESSANT COMPOSITIONS CONTAINING THE SAME

The present invention relates to novel peptides, process for preparing the peptides and psychodepressant compositions containing the peptide.

When amino acids, peptides, protective groups, active groups, etc. are represented by symbols in this specification and appended claims, usual symbols as defined by IUPAC and IUB or as used in the art are employed. When an optical isomer or isomers of a particular amino acid or the like referred to can exist, the symbol concerned represents the L-isomer, D-isomer and/or racemate. Examples of symbols are given below.

| | |
|---|---|
| Tyr | tyrosine |
| Met | methionine |
| Gly | glycine |
| Trp | tryptohan |
| Asp | aspartic acid |
| Phe | phenylalanine |
| pGlu | pyroglutamic acid |
| Z | benzyloxycarbonyl group |
| Boc | tert-butyloxycarbonyl group |
| Me | methyl group |
| Bz | benzyl group |
| OSu | succinimidoxy group |
| Suc | $HOOC-CH_2CH_2-CO-$ |
| Glt | $HOOC-(CH_2)_3-CO$ |
| Pht |  |

The peptides of the present invention are novel and are represented by the formula (1)

$$R-Tyr(SO_3H)-Met-Gly-Trp-Met-Asp-W-NH_2 \quad (1)$$

wherein R is HOOC—A—CO—Asp— (wherein A is lower alkylene), pGlu—Asp—, HOOC—A—CO— (wherein A is lower alkylene) or

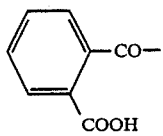

and W is Phe or $N^\alpha$-lower alkyl-Phe.

Examples of lower alkylene groups represented by A in the formula (1) are alkylene groups having 1 to 6 carbon atoms, such as methylene, ethylene, 1-methyltrimethylene, 2-methyltrimethylene, trimethylene, tetramethylene, pentamethylene and hexamethylene. Exemplary of the lower alkyl in $N^\alpha$-lower alkyl-Phe represented by W are alkyl groups having 1 to 6 carbon atoms, such as methyl, ethyl, propyl, isopropyl, butyl, isobutyl, tert-butyl, pentyl and hexyl. The carboxyl substituent in

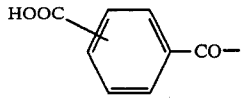

may be in the o-position, m-position or p-position. A particular group represented by $N^\alpha$-lower alkyl-Phe will be hereinafter represented by the first two letters of the alkyl therein, followed by Phe. For instance, a group represented by $N^\alpha$-lower alkyl-Phe wherein the lower alkyl is methyl is expressed by "MePhe", while one wherein the lower alkyl is ethyl is represented by "EtPhe".

Among the compounds of the formula (1), a preferred class of compounds are peptides represented by the formula $$R-Tyr(SO_3H)-Met-Gly-Trp-Met-Asp-Phe-NH_2 \quad (1a)$$

wherein R is $HOOC(CH_2)_3CO$—Asp or pGlu—Asp—, and salts thereof. The compounds of the formula (1) further includes another preferred class of compounds which are represented by the formula $$R-Tyr(SO_3H)-Met-Gly-Trp-Met-Asp-W-NH_2 \quad (1b)$$

wherein R is HOOC—A—CO— (wherein A is lower alkylene) or

and W is Phe or $N^\alpha$-lower alkyl-Phe, and salts thereof.

The peptides of the invention have outstanding activity to suppress the central nervous system. More specifically, the peptides of the invention inhibit the hyperlocomotion in mice which is induced by a thyrotropin releasing hormone (TRH) or methamphetamine given to the animals. The peptides also inhibit apomorphine-induced climbing behavior and methamphetamine-induced stereotypy in mice, inhibit the responding under fixed ratio schedule in rats, significantly extends the duration of anesthesia produced in mice by the administration of pentobarbital or halothane, and accelerate the metabolism of dopamine in a certain area of the brain in rats. In testing mice for L-dopa potentiation or for excitatory reaction induced by the administration of L-dopa and pargyline which is a monoamine oxidase inhibitor, the present peptides inhibit the excitatory reaction in mice, thus acting against dopamine. In addition to the foregoing effects, the present peptides have other effects, such as hypothermic, antispasmodic or analgesic effects.

Known peptides which are similar in chemical structure to the peptides of the present invention include, for example, peptide (hereinafter referred to as "CCK-8") of the following formula.

$$Asp-Tyr(SO_3H)-Met-Gly-Trp-Met-Asp-Phe-NH_2 \quad (2)$$

However, the present peptides have a higher action against dopamine than CCK-8 in respect of the following. (a) Although the present peptides inhibit the apomorphine-induced climbing behavior in mice, CCK-8 does not inhibit this behavior. (b) Unlike the peptides of the present invention, CCK-8 does not accelerate the metabolism of dopamine in the brain of rats. (c) In experiments of yawning behavior which is thought to be induced by a reduction in the amount of dopamine, CCK-8 induces no yawning behavior whatsoever, whereas the present peptides induce the yawning behavior. (d) The yawning behavior resulting from the administration of apomorphine which is a dopamine receptor agonist is inhibited by the present peptides but is not inhibited by CCK-8. Accordingly the present peptides are more effective than CCK-8 on chronic schizophrenic symptoms, especially autistic symptoms, on which conventional anti-schizophrenic drugs are ineffective. In respect of side effects, moreover, CCK-8 induces catalepsy in test animals, whereas the present peptides induce no catalepsy. It is therefore thought that the present peptides do not produce extrapyramidal side effects which are attendant on conventional antischizophrenic drugs. Thus the present peptides are useful as a psychodepressant drug, and especially very effective for curing schizophrenia.

The peptides of the present invention represented by the formula (1) can be prepared by processes which are usually used for the synthesis of peptides, more specifically by the processes described in "The Peptides", Vol. 1 (1966), by Schröder and Luhke, Academic Press, New York, U.S.A. or in "Synthesis of Peptides", by Izumiya et al, Maruzen Co., Ltd., Tokyo, 1975. Examples of such processes are the azide method, the acid chloride method, the acid anhydride method, the mixed anhydride method, the DCC method, the active ester method (p-nitrophenyl ester method, N-hydroxysuccinimido ester method, cyanomethyl ester method, etc.), the method wherein Woodward's reagent K is used, the carbodiimidazole method, the oxidation-reduction method, the DCC/additive (HONB, HOBt) method, the solid phase method, etc.

The peptide of the formula (1) is prepared usually by one of the above conventional processes for synthesizing polypeptides, for example, by the stepwise method wherein amino acids are coupled one by one in succession to the terminal amino acid by condensation, or by coupling several divided segments. More specifically, for the two fragments divided at an optional position of coupling of the peptide to be prepared, two starting materials are prepared: one corresponding to one of the fragments and having a reactive carboxyl group, and the other corresponding to the other fragment and having a reactive amino group. These starting materials are subjected to condensation by a conventional method of peptide synthesis, and when the resulting product has a protective group, the protective group is removed in the usual manner. When aspartic acid is used in the reaction for producing the peptide of the formula (1), it is generally desirable to have this particular acid protected before the reaction. In the final step, all the protective groups are usually removed from the protected peptide wherein at least one of the constituent amino acid residues is protected.

In the reaction process for synthesizing the peptide of the formula (1), the functional group which should not participate in the reaction is protected by a usual protective group, which is removed after the reaction. The functional groups which participate in the reaction are usually activated. The reaction methods involved in the synthesis are known, and the reagents, etc. to be used therefor are suitably selected from those already known.

Examples of useful protective groups for the amino group are Z, Boc, tert-amyloxycarbonyl, isobornyloxycarbonyl, p-methoxybenzyloxycarbonyl, 2-chlorobenzyloxycarboxyl, adamantyloxycarboxyl, trifluoroacetyl, phthalyl, formyl, o-nitrophenylsulfenyl, diphenylphosphinothioyl, etc. Examples of useful protective groups for the carboxyl group are alkyl (e.g., methyl, ethyl, propyl, butyl, tert-butyl and like alkyl), benzyl, p-nitrobenzyl, p-methoxybenzyl, p-chlorobenzyl, benzhydryl, carbobenzoxyhydrazino, tert-butyloxycarbonylhydrazino, tritylhydrazino, etc.

Examples of activated carboxyl groups are corresponding acid chloride, acid anhydride or mixed anhydride, azido, active esters (esters with pentachlorophenol, p-nitrophenol, N-hydroxysuccinimide, N-hydroxybenztriazole, N-hydroxy-5-norbornene-2,3-dicarboxyimide, etc.) and the like. In some cases, the peptide coupling forming reaction can be carried out in the presence of a condensation agent such as dicyclohexylcarbodiimide (D.C.C.), carbodiimidazole or like carbodiimide reagent or tetraethylpyrophosphide, etc.

The peptide of the formula (1) has an acyl group (Suc, Glt, Pht or the like) at its N-terminal and a masked α-amino group. Most preferably the peptide is prepared by synthesizing a peptide represented by the formula

R—Tyr—Met—Gly—Trp—Met—Asp—W—NH$_2$     (3)

wherein R and W are as defined above by one of the above processes, and thereafter subjecting the peptide of the formula (3) to sulfuric acid esterification to convert the Tyr group to Tyr(SO$_3$H). This process including the final step of sulfuric acid esterification has the advantage of inhibiting cleavage of the sulfuric acid ester bond to the greatest possible extent, and reducing formation of by-product, unlike the process wherein an intermediate product having a protective group or groups is prepared first by one of the foregoing processes and then subjected to sulfuric acid esterification, followed by the step of removing the protective group, acylation step and the step of extending peptide chain. Thus the process has the advantage of giving the desired product in higher yield with higher purity.

The sulfuric acid esterification is known and can be carried out with use of a usual sulfating reagent, such as pyridine-sulfuric anhydride complex (H. C. Reitz et al., J. Am. Chem. Soc., 68, 1031 (1946)). More specifically, the reaction is conducted, for example, by dissolving a peptide of the formula (3) in dimethylformamide, pyridine or like inert solvent, and adding to the resulting solution the pyridine-sulfuric anhydride complex in about 10 times the amount of the peptide. Preferably the reaction is conducted at a low temperature first and then at room temperature for 15 to 20 hours.

The peptide of the formula (1) thus prepared can be desalted and purified by usual methods. For example, the product can be purified by ion-exchange chromatography with use of DEAE-cellulose or the like, partition chromatography with use of Sephadex LH-20, Sephadex G-25 or the like, reverse phase chromatography with use of ODS-silica gel or the like, normal phase chromatography with use of silica gel or the like, or high-performance liquid chromatography (HPLC).

The product can also be purified by the method disclosed in Published Unexamined Japanese Patent Application No. 4953/1981 or Published Examined Japanese Patent Application No. 22474/1983, i.e., by concentrating the esterification reaction mixture, adding to the concentrate methanol, butanol, ethanol, dimethylformamide, water or like solvent and an aqueous solution of water-soluble salt of calcium, zinc or like bivalent metal to stabilize the peptide amide sulfate ester as a bivalent metal salt and, at the same time, to precipitate the sulfuric acid resulting from the unreacted pyridinesulfuric acid complex as an insoluble bivalent metal sulfate, removing the precipitate and purifying the liquid phase. This method is also suitable for the stabilization of the sulfuric acid ester and prevention of side reaction.

The peptide of the formula (3) can be prepared by known peptide synthesizing processes. When R is HOOC—A—CO—Asp— wherein A is as defined above or pGlu—Asp—, the peptide can be produced, for example, by removing the protecting group from protected hexapeptide, Boc—Met—Gly—Trp—Met—Asp—Phe—NH$_2$ (M. A. Ondetti et al. Journal of the American Chemical Society 92, 195 (1970)), with use of trifluoroacetic acid or like acid, and coupling R—Tyr—NHNH$_2$ wherein R is as defined above to the unprotected peptide by the azide process for condensation. Further, the peptide of the formula (3) can be prepared by reacting anhydride of acid, HOOC—A—COOH wherein A is as defined above, or an active ester of pyroglutamic acid with octapeptide, H—Asp—Tyr—Met—Gly—Trp—Met—Asp—Phe—NH$_2$ (M. A. Ondetti et al. Journal of the American Chemical Society 92, 195 (1970)). Further, when R is HOOC—A—CO— wherein A is as defined above or

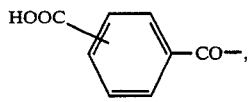

the peptide of the formula (3) can be prepared by removing the protecting group from the protected hexapeptide, Boc—Met—Gly—Trp—Met—Asp—Phe—NH$_2$, with trifluoroacetic acid or like acid, reacting the resulting unprotected hexapeptide with Boc—Tyr—Osu to obtain Boc—Tyr—Met—Gly—Trp—Met—Asp—Phe—NH$_2$, removing the protecting group from the resulting product with trifluoroacetic acid or like acid, and reacting the resulting unprotected product with anhydride of acid, HOOC—A—COOH wherein A is as defined above, or phthalic anhydride.

For the production of a peptide of the formula (1) wherein W is N$^\alpha$-lower alkyl-Phe, a corresponding N$^\alpha$-substituted amino acid can be prepared, for example, by reacting an N$^\alpha$-protected amino acid, e.g., Z—Phe—OH or the like, with potassium hydride, sodium hydride or the like in the presence of a suitable crown ether at about 0° C. for about 1 hour, and reacting a suitable alkyl halide, such as methyl iodide or ethyl iodide, with the resulting product at about 0° C., with stirring for 2 days after dropwise addition of the halide over a period of about 30 minutes. Further the N$^\alpha$-substituted amino acid wherein the substituent is methyl can be prepared, for example, by reacting an amino acid (Phe) with benzaldehyde, treating the resulting Schiff base with a suitable reducing agent, such as NaBH$_4$, to obtain N-monobenzylamino acid, reacting formic acid or formaldehyde with the acid, and subjecting the product to hydrogenation catalytic reduction reaction in the presence of a palladium catalyst or the like (see P. Quitt et al., Helve. Chim. Acta., 46, 327 (1963)).

When desired, the peptide of the formula (1) thus obtained can be converted to pharmaceutically acceptable salts, such as salts of sodium, potassium and like alkali metals, salts of calcium and like alkaline earth metals, salts of triethylamine, ammonium and like amines, etc.

The psychodepressant compositions containing a peptide of the formula (1) or a salt thereof according to the invention as an active component is prepared with use of a known pharmaceutical carrier. Examples of useful carriers are those usually used for preparing medicinal compositions in the desired form, such as diluents and excipients including filler, extender, binder, wetting agent, disintegrator, surfactant, glazing agent, etc.

The psychodepressant compositions can be in any of various dosage forms in accordance with the contemplated purpose of treatment. Typically they are in the form of tablets, pills, powders, solutions, suspensions, emulsions, granules, capsules, suppositories, injections (solutions, suspensions, etc.), ointments, nasal preparations, etc. Suppositories, injections and nasal preparations are preferred. Examples of useful carriers for preparing tablets are excipients such as lactose, white sugar, sodium chloride, glucose solution, urea, starch, calcium carbonate, kaolin, crystalline cellulose and silicic acid; binders such as water, ethanol, propanol, syrup, glucose, starch solution, gelatin solution, carboxymethylcellulose, shellac, methylcellulose, potassium phosphate and polyvinylpyrrolidone; disintegrators such as dried starch, sodium alginate, agar powder, laminaria powder, sodium hydrogencarbonate, calcium carbonate, Tween, sodium lauryl sulfate, glyceryl monostearate, starch and lactose; disintegration suppressants such as white sugar, stearin, cacao butter and hydrogenated oils; absorption promoters such as quaternary ammonium salt and sodium lauryl sulfate; humectants such as glycerin and starch; adsorbents such as starch, lactose, kaolin, bentonite and colloidal silicic acid; glazing agents such as purified talc, stearic acid salts, boric acid powder and polyethylene glycol; etc. Examples of useful carriers for preparing pills are excipients such as glucose, lactose, starch, cacao fat, hardened vegetable oils, kaolin and talc; binders such as gum arabic powder, tragacanth powder, gelatin and ethanol; disintegrators such as laminaria and agar; etc. When desired, tablets can be provided with a usual coating. Thus useful are sugar-coated, gelatin-coated, enteric coated, film-coated, double-layer and multiple-layer tablets. Suppositories may be formulated with use of a wide variety of known carriers, such as polyethylene glycol, cacao fat, higher alcohols, esters of higher alcohols, gelatin, and semisynthetic glycerides. The solutions, emulsions and suspensions for injection should be sterilized and are preferably isotonic with the blood. For the preparation of such solutions, emulsions and suspensions, any diluent is usable which is usually used in the art. Examples of useful diluents are water, ethyl alcohol, propylene glycol, ethoxylated isostearyl alcohol, polyoxyisostearyl alcohol, polyoxyethylene sorbitol, sorbitan esters and the like. For the preparation of solutions, sodium chloride, glucose or glycerin may be incorporated therein in an amount sufficient to render the solutions isotonic. Such solutions may further incorporate usual solubilizing agents, buffers, analgesics, preservatives, etc. The present compositions may contain coloring agents, preservatives, perfumes, flavoring agents, sweetening agents, etc. as well as other drugs.

The amount of the peptide of the formula (1) or salt thereof to be contained in the psychodepressant compositions is not specifically limited but can be suitably determined over a wide range. Usually the amount is about 1 to about 70% by weight of the whole composition.

The psychodepressant compositions are not specifically limited in the mode of administration but can be given by a suitable method in accordance with the particular form of the composition. For example, tablets, pills, solutions, suspensions emulsions, granules and capsules are administered orally. Injections are given intravenously, singly or as admixed with an auxiliary solution of glucose, amino acids, etc. When desired, injections are singly given intramuscularly, intradermally, subcutaneously or intraperitoneally. Suppositories are given to the rectum, while nasal preparations are administered through the nostril.

The psychodepressant compositions of the present invention are given at a dose suitably determined according to the purpose, symptoms, etc. Usually the compositions are administered in a daily dose of about 4 μg to about 2 mg per kg of body weight, calculated as the peptide of the formula (1) or a salt thereof, for human patients. The composition is given in three to four divided doses daily. The composition may be given every week or two.

The present invention will be described below with reference to preparation examples, in which the amino acids are all L-isomers when optical isomers can be present.

EXAMPLE 1

Preparation of
Glt—Asp—Tyr($SO_3H$)—Met—Gly—Trp—Met—Asp—Phe—$NH_2$ (i) A 16.5 g quantity of H—Asp—Tyr—Met—Gly—Trp—Met—Asp—Phe—$NH_2$ was dissolved in 200 ml of dimethylformamide containing 4.4 ml of triethylamine, and 3.55 g of glutaric anhydride was added to the solution with ice-cooling. After stirring the mixture at 4° C. for 17 hours, the solvent was distilled off at reduced pressure, and the residue was solidified with 1N citric acid and washed with water. The product was recrystallized from 200 ml of methanol, giving 17.26 g of Glt—Asp—Tyr—Met—Gly—Trp—Met—Asp—Phe—$NH_2$. Yield 94.6%.

(ii) A 1.18 g quantity of the acylated peptide obtained by the procedure (i) was dissolved in 20 ml of dimethylformamide and 2 ml of pyridine, and 1.59 g of pyridinesulfuric anhydride complex (product of Aldrich Chemical Co., Inc., U.S.A.) was added to the solution with ice-cooling. The mixture was stirred at 0° C. for 30 minutes and further at room temperature for 20 hours. The reaction mixture was concetrated in vacuo, 50 ml of 0.05M aqueous ammonium carbonate solution was added to the residue, and the solution was adjusted to a pH of 8.5 with ammonia water. The solution was then applied to a column (4 cm×12 cm) of DEAE-Cellulose (product of Brown Co., U.S.A.), washed with 1.5 liters of 0.05M ammonium carbonate-ammonium bicarbonate buffer (pH 8.5) and then eluted with 2 liters of 0.2M of the same buffer (pH 8.5). The desired fraction was collected, concentrated and lyophilized to give 801 mg of Glt—Asp—Tyr($SO_3H$)—Met—Gly—Trp—Met—As-

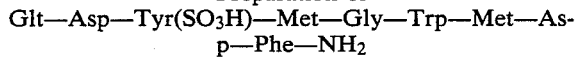
p—Phe—$NH_2$ (hereinafter referred to as "peptide A"), yield 66.4%.

Elementary analysis (for $C_{54}H_{68}N_{10}O_{19}S_3 \cdot NH_3 \cdot 4H_2O$); Calcd: C, 48.17%; H, 5.91%; N, 11.44%; Found: C, 47.97%; H, 5.68%; N, 11.73%.

Result of amino acid analysis by acid decomposition; Asp 1.98 (2), Gly 1.05 (1), Met 2.08 (2), Tyr 0.98 (1), Phe 0.94 (1).

Infrared absorption spectrum revealed a strong peak peculiar to sulfuric acid ester at 1050 cm$^{-1}$.

EXAMPLE 2

Preparation of
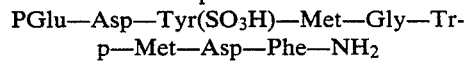
PGlu—Asp—Tyr($SO_3H$)—Met—Gly—Trp—Met—Asp—Phe—$NH_2$ (i) A 10.27 g quantity of Boc—Met—Gly—Trp—Met—Asp—Phe—$NH_2$ was dissolved in 30 ml of trifluoroacetic acid in the presence of 0.2 ml of ethanedithiol and treated at room temperature for 30 minutes. Anhydrous ether (200 ml) was added to the solution for precipitation, followed by filtration and drying. A solution of the hexapeptide in 100 ml of dimethylformamide containing 1.63 ml of triethylamine was reacted with the azide derived from 7.32 g of pGlu—Asp—Tyr—$NHNH_2$ (m.p. 213°–215° C., elementary analysis: calcd. for $C_{18}H_{23}N_5O_7 \cdot H_2O$: C, 49.20%, H, 5.73%, N, 15.94%; found: C, 49.08%, H, 5.51%, N, 15.94%) with use of isoamyl nitrite. After removing the solvent from the reaction mixture in vacuo, the residue was solidified with addition of 1N citric acid and washed with water. The product was recrystallized from dimethylformamidemethanol, giving 9.66 g of pGlu—Asp—Tyr—Met—Gly—Trp—Met—Asp—Phe—$NH_2$, yield 70.9%.

(ii) A 4.70 g quantity of nonapeptide obtained by the procedure (i) was dissolved in 100 ml of dimethyl formamide and 10 ml of pyridine, 6.37 g of pyridinesulfuric anhydride complex was added to the solution with ice-cooling, and the mixture was stirred at 0° C. for 30 minutes and further at room temperature for 17 hours. The reaction mixture was concetrated in vacuo, 200 ml of 0.05M ammonium carbonate was added to the residue, and the solution was adjusted to a pH of 8.5 with ammonia water. The solution was purified in the same manner as in Example 1 by DEAE-Cellulose (5 cm×25 cm) ion-exchange chromatography. The active fraction was collected, then concentrated and freeze-dried, giving 3.309 g of pGlu—Asp—Tyr($SO_3H$)—Met—Gly—Trp—Met—Asp—Phe—$NH_2$ (hereinafter referred to as "peptide B"), yield 66.0%.

Elementary analysis (for $C_{54}H_{67}N_{11}O_{18}S_3 \cdot NH_3 \cdot 4H_2O$)

| Calcd: | C, 48.28%; | H, 5.85%; | N, 12.51% |
| Found: | C, 48.23%; | H, 5.45%; | N, 12.39% |

Result of amino acid analysis by acid decomposition

| Asp 1.97 (2), | Glu 0.98 (1), | Gly 1.04 (1) |
| Met 2.15 (2), | Tyr 0.97 (1), | Phe 0.94 (1) |

Infrared absorption spectrum: 1050 cm$^{-1}$.

PHARMACOLOGICAL TEST 1

Effect on hyperlocomotion induced by thyrotropin releasing hormone (TRH)

Male ddy mice (weighing 18 to 24.5 g) were used. The mice were placed into a transparent acrylic resin cage (26×37×11 cm) installed on Animex meter. Before experiment, the mice were allowed to habituate for 2 hours in the cage to fully lower the activity of the mice. After the completion of habituation, peptide A, peptide B or a diluent (physiological saline containing 1 mg/ml of sodium hydrogencarbonate) serving as a control was subcutaneously given to the mice. Thirty minutes thereafter, 5 mg/kg of TRH was intraperitoneally given to the animals. The activity counts during the period of 60 minutes following the administration of TRH was measured. Student's t-test was resorted to for statistical treatment. Table 1 shows the results.

TABLE 1

| Test compound | Dose (mg/kg) | Activity counts (frequency per 60 min): Mean ± S.E. |
| --- | --- | --- |
| Peptide A | 0.1 | 936 ± 115 |
|  | 0.3 | 613 ± 114 |
|  | 1 | 148 ± 34 |
| Peptide B | 0.03 | 1009 ± 165 |
|  | 0.1 | 601 ± 78 |
|  | 0.3 | 626 ± 143 |
| Control | — | 1215 ± 114 |

Table 1 shows that peptide A and peptide B inhibit the hyperlocomotion induced by TRH.

PHARMACOLOGICAL TEST 2

Effect on climbing behavior induced by apomorphine

Male ddy mice (weighing 20 to 30 g) were used, with 10 mice in each group. Each mouse was placed into a cylindrical cage, 12 cm in diameter and 14 cm in height, made up of vertical rods of 2 mm in diameter spaced apart at a distance of 10 mm in a circular arrangement. The mouse was allowed to stand therein for 2 hours. Peptide A, peptide B, CCK-8 or, as a control, the above-mentioned diluent was subcutaneously given to the animal, and 30 minutes later, 0.75 mg/kg of apomorphine was subcutaneously given. Ten minutes, 15 minutes, 20 minutes, 25 minutes, 30 minutes, 35 minutes and 40 minutes after the administration of apomorphine, the animal was observed for 1 minute to obtain 7 scores according to the following criteria and total the seven scores. The test was carried out in soundproof compartments.

0: All the four legs are on the floor.
1: Forelegs are on rods.
2: At least three legs are on rods.

Student's t-test was resorted to for statistical treatment. Table 2 shows the results.

TABLE 2

| Test compound | Dose (mg/kg) | Average: Mean ± S.E. (total of 7 scores) |
| --- | --- | --- |
| Peptide A | 0.01 | 8.6 ± 0.6 |
|  | 0.03 | 7.9 ± 0.6 |
|  | 0.1 | 5.3 ± 0.5 |
|  | 0.3 | 5.1 ± 0.7 |
|  | 1 | 4.5 ± 1.0 |
| Peptide B | 0.01 | 8.7 ± 0.8 |
|  | 0.1 | 5.4 ± 0.8 |
|  | 1 | 4.7 ± 1.1 |
| CCK-8 | 0.01 | 10.2 ± 0.7 |
|  | 0.1 | 11.4 ± 0.6 |
|  | 1 | 9.5 ± 1.0 |
| Control | — | 9.8 ± 0.7 |

Table 2 reveals that peptide A and peptide B inhibit the climbing behavior whereas CCK-8 produces little or no influence on the climbing behavior.

PHARMACOLOGICAL TEST 3

Effect on metabolism of amine in the brain

Unfasted male Wister rats (weighing 180 to 220 g) were used. Peptide A or peptide B was subcutaneously given to the animal at a dose of 1 mg/kg, the head was irradiated with microwave 1 hour thereafter, and amine metabolite was extracted from the brain. First, removed tissues were homogenized with 1M formic acid and centrifuged at 20,000×g for 20 minutes, and the supernatant (1 ml) was shaken with 5 ml of ethyl acetate. The 3,4-dihydroxyphenylacetic acid (DOPAC), homovanillic acid (HVA) and 5-hydroxyindoleacetic acid (5-HIAA) in the ethyl acetate layer were analyzed by high-performance liquid chromatography under the following conditions. Chemcosorb, 5-ODS, 20 cm×4.6 mm I.D. was used for a separating column, and a mobile phase (0.1M $KH_2PO_4$ (pH 5.0)-5 mM EDTA-2Na-5% acetonitrile) was passed through the column at a flow rate of 1 ml/min. The electrochemical detector was set to an oxidation potential of +0.8 V.

Neither of peptide A and peptide B was found to influence the content of metabolite in frontal cortex, limbic forebrain, and striatum, but these peptides significantly increased the DOPAC content by about 60% in hypothalamus.

PHARMACOLOGICAL TEST 4

Effect on yawning behavior

Male Wister rats (weighing 200 to 300 g) were used, with 10 rats in each group. The rat was placed into a plastics cage (17×24×12 cm) with a floor mat and was then habituated for 30 minutes. Peptide A, peptide B, CCK-8 or the above-mentioned diluent serving as a control was subcutaneously given to the animal. Thirty minutes thereafter, 0.03 mg/kg of apomorphine was subcutaneously given to the animal. The number of yawns induced by apomorphine was counted during a period of 30 minutes following administration of apomorphine. The test was conducted in a soundproof compartment for each animal. Wilcoxon rank-sum test was resorted to for statistical treatment. Table 3 shows the results.

TABLE 3

| Test compound | Dose (mg/kg) | Number of yawns (average) |
| --- | --- | --- |
| Peptide A | 0.3 | 1.5 |
|  | 1 | 0 |
| Peptide B | 1 | 1.0 |
| CCK-8 | 1 | 4.9 |
| Control | — | 4.5 |

Table 3 shows that peptide A and peptide B inhibit the yawning behavior induced by apomorphine.

EXAMPLE 3

Preparation of
Suc—Tyr(SO3H)—Met—Gly—Trp—Met—Asp—MePhe—NH2

(1) Synthesis of MePhe—NH2

The procedure of the process of P. Quitt et al. (Helv. Chim. Acta, 46, 327 (1963)) was followed. A 16.5 g quantity (0.1 mole) of Phe was dissolved in 50 ml of 2N aqueous NaOH solution, 10.1 ml of benzaldehyde was added to the solution with ice-cooling, and the mixture was stirred for about 10 minutes to obtain a uniform reaction mixture. To the mixture was added 1.14 g of NaBH4 in small portions at a temperature of up to 15° C., and the mixture was stirred for 30 minutes. The above procedure was repeated 3 times with use of benzaldehyde and NaBH4, each in one-half the above amount. The reaction mixture was stirred for 2 hours and then washed with ether. The aqueous layer was neutralized with 1N HCl with ice-cooling, and the resulting precipitate was filtered off and dried. The product was recrystallized from a mixture of 50 ml of dimethylformamide (DMF) and 200 ml of methanol to obtain 20.73 g of $N^\alpha$-benzyl-phenylalanine (BzPhe), yeild 81.2%. M.p. 250°–253° C.

$[\alpha]_D^{24} = +20.2°$ (C=1, 0.2N NaOH)

Elementary analysis (for $C_{16}H_{17}NO_2$)

|              | C      | H     | N    |
|--------------|--------|-------|------|
| Calcd. (%):  | 75.27, | 6.71, | 5.49 |
| Found (%):   | 75.19, | 6.67, | 5.50 |

To a 12.77 g portion of the foregoing Bz—Phe were added 16.8 ml of formic acid and 15.0 ml of 37% formaldehyde, and the mixture was refluxed with heating at 110° C. for 4 hours. The reaction mixture was allowed to cool and then concentrated in vacuo. Water was added to the concentrate to obtain a precipitate, which was then filtered off and recrystallized from 200 ml of hot water, giving 12.86 g of N-benzyl-N-methyl-phenylalanine (BzMePhe), yield 95.5%. M.p. 214°–215° C.

$[\alpha]_D^{24} = -8.7°$ (C=1, 0.2N NaOH)

Elementary analysis (for $C_{17}H_{19}NO_2$)

|              | C      | H     | N    |
|--------------|--------|-------|------|
| Calcd. (%):  | 75.81, | 7.11, | 5.20 |
| Found (%):   | 75.78, | 7.05, | 5.15 |

A 12.66 g portion of the BzMePhe was dissolved in 120 ml of acetic acid and 47 ml of HCl, and the solution was subjected to hydrogen catalytic reduction (room temperature, 8 hours) with addition of 5.0 g of 10% palladium-carbon catalyst. After separating off the catalyst by filtration, the filtrate was concentrated in vacuo, and the concentrate was recrystallized from ethanol (50 ml)-ether (500 ml) to give 7.93 g of MePhe, yeild 94.1%. M.p. 225° C.

$[\alpha]_D^{24} = +49.3°$ (C=1, 1N NaOH)

Elementary analysis (for $C_{10}H_{13}NO_2$)

|              | C      | H     | N    |
|--------------|--------|-------|------|
| Calcd. (%):  | 67.02, | 7.31, | 7.82 |
| Found (%):   | 66.87, | 7.41, | 7.68 |

A 7.88 g (0.044 mole) portion of the MePhe was cooled to −20° to −30° C. in methanol, 5.76 g of thionyl chloride was slowly added thereto, and the mixture was stirred overnight at room temperature. The mixture was concentrated in vacuo, and the concentrate was crystallized from methanol-ether to obtain 9.67 g of MePhe—OCH3 (hydrochloride). M.p. 143°–145° C.

$[\alpha]_D^{24} = +16.4°$ (C=2, H2O)

Elementary analysis (for $C_{11}H_{16}NO_2Cl$)

|              | C      | H     | N    |
|--------------|--------|-------|------|
| Calcd. (%):  | 57.52, | 7.02, | 6.10 |
| Found (%):   | 57.37, | 7.18, | 6.16 |

A 9.19 g portion of the methyl ester was dissolved in methanol. Ammonia gas was passed through the solution for 1 hour while cooling the solution with dry ice-ethanol. The mixture was thereafter sealed off and allowed to stand at room temperature for 2 days. Subsequently the solvent was distilled off in vacuo, and the residue was crystallized from ether to give 5.72 g of MePhe—NH2, yeild 80.2%. M.p. 155°–157° C.

$[\alpha]_D^{24} = +28.6°$ (C=1, methanol)

Elementary analysis (for $C_{10}H_{14}N_2O$)

|              | C      | H     | N     |
|--------------|--------|-------|-------|
| Calcd. (%):  | 67.39, | 7.92, | 15.72 |
| Found (%):   | 67.83, | 7.99, | 15.68 |

(2) Synthesis of Z—Asp(OBz)—MePhe—NH2

A 16.08 g quantity of Z—Asp(OBz)—OH was dissolved in 50 ml of tetrahydrofuran (THF), and the solution was cooled to −20° C. To the solution were added 4.95 ml of N-methylmorpholine and 5.94 ml of isobutyl chloroformate. The resulting mixed anhydride was added to a solution of 5.34 g of the MePhe—NH2 obtained by the procedure (1) in 50 ml of dimethylformamide (DMF, containing 4.2 ml of triethylamine). The mixture was stirred at 0° C. for 30 minutes and then at room temperature for 1 hour. The solvent was distilled off in vacuo, 300 ml of ethyl acetate was added to the residue, and the acetate layer was washed with 1N citric acid, saturated sodium chloride solution, saturated sodium hydrogencarbonate solution and saturated sodium chloride solution (with 300 ml of each, three times) in succession. The organic layer was dried over anhydrous sodium sulfate. After distilling off the solvent from the layer, the residue was dissolved in 50 ml of chloroform. The solution was purified by silica gel column (4 cm×28 cm) chromatography. The resulting fraction was concentrated in vacuo, and the concentrate was crystallized from methanol-water, affording 11.99 g of Z—Asp(OBz)—MePhe—NH2, yield 77.2%. M.p. 131°–133° C.

$[\alpha]_D^{24} = -91.1°$ (C=1, DMF)

Elementary analysis (for $C_{29}H_{31}N_3O_6$)

|  | C | H | N |
|---|---|---|---|
| Calcd. (%): | 67.30, | 6.04, | 8.12 |
| Found (%): | 67.38, | 6.23, | 8.05 |

(3) Synthesis of Boc—Met—Asp—MePhe—NH$_2$

A 6.45 g quantity (0.0125 mole) of Z—Asp—MePhe—NH$_2$ obtained by the procedure (2) was subjected to hydrogen catalytic reduction in 200 ml of methanol containing 12.5 ml of 1N hydrochloric acid in the presence of 2.2 g of 10% palladium-carbon catalyst (room temperature, 6 hours). After filtering off the catalyst, the solvent was distilled off from the reaction mixture to obtain an unprotected dipeptide, with which 3.74 g of Boc—Met—OH was reacted in the same manner as in the procedure (2) for condensation (with stirring at 0° C. for 10 hours, at 40° C. for 1 minute and at room temperature for 20 minutes). Concentration of the reaction mixture in vacuo was followed by extraction with ethyl acetate and crystallization from methanol-ether, giving 4.50 g of Boc—Met—Asp—MePhe—NH$_2$, yield 68.8%. M.p. 94°-96° C.

$[\alpha]_D^{24} = -75.7°$ (C=1, DMF)

Elementary analysis (for $C_{24}H_{36}N_4O_7S$)

|  | C | H | N |
|---|---|---|---|
| Calcd. (%): | 54.95, | 6.92, | 10.68 |
| Found (%): | 54.85, | 6.79, | 10.26 |

(4) Synthesis of Boc—Trp—Met—Asp—MePhe—NH$_2$

A 5 ml quantity of trifluoroacetic acid containing 0.2 ml of ethanedithiol was added to 1.73 g (0.0033 mole) of the Boc—Met—Asp—MePhe—NH$_2$ obtained by the procedure (3), the mixture was allowed to stand at room temperature for 30 minutes, 100 ml of anhydrous ether was added thereto, and the resulting solid precipitate was filtered off and dried. The protection-removed tripeptide thus obtained was dissolved in 50 ml of DMF, the solution was neutralized with 0.46 ml of triethylamine, and 1.99 g of Boc—Trp—OSu was further added to the solution. The mixture was stirred overnight at room temperature. The reaction mixture was concentrated in vacuo, and the concentrate was solidified with addition of 1N citric acid, washed with water and crystallized from ethanol to give 1.54 g of Boc—Trp—Met—Asp—MePhe—NH$_2$, yield 65.6%. M.p. 138°-140° C.

Elementary analysis (for $C_{35}H_{46}N_6O_8S$)

|  | C | H | N |
|---|---|---|---|
| Calcd. (%): | 59.14, | 6.52, | 11.82 |
| Found (%): | 59.01, | 6.49, | 12.06 |

(5) Synthesis of Boc—Met—Gly—Trp—Met—Asp—MePhe—NH$_2$

In the same manner as in the procedure (4), the protection was removed with use of trifluoroactic acid from 1.20 g (1.7 mmole) of Boc—Trp—Met—Asp—MePhe—NH$_2$ obtained by the procedure (4).

On the other hand, a solution of 0.817 g of Boc—Met—Gly—NHNH$_2$ in 20 ml of DMF was cooled to −20° C. or lower, and 2.13 ml of 6N HCl-dioxane and 0.36 ml of isoamyl nitrite were added to the solution to obtain an azide compound. The reaction mixture was neutralized with 1.75 ml of triethylamine and then added to a solution of the protection-removed tetrapeptide and 0.24 ml of triethylamine in 20 ml of DMF. The resulting mixture was stirred at −20° C. for 2 hours and then at 4° C. for 17 hours. The reaction mixture obtained was treated in the same manner as in the procedure (4) to give 0.97 g of Boc—Met—Gly—Trp—Met—Asp—MePhe—NH$_2$, yield 63.5%. M.p. 134°-136° C.

Elementary analysis (for $C_{42}H_{58}N_8O_{10}S_2$)

|  | C | H | N |
|---|---|---|---|
| Calcd. (%): | 56.11, | 6.50, | 12.46 |
| Found (%): | 55.95, | 6.47, | 12.43 |

(6) Synthesis of Boc—Tyr—Met—Gly—Trp—Met—Asp—MePhe—NH$_2$

A 0.88 g quantity (0.98 mmole) of the Boc—Met—Gly—Trp—Met—Asp—MePhe—NH$_2$ obtained by the procedure (5) and 0.74 g of Boc—Tyr—Osu were subjected to condensation reaction in the same manner as in the procedure (4), and the product obtained was recrystallized from methanol-ether, giving 0.89 g of Boc—Tyr—Met—Gly—Met—Asp—MePhe—NH$_2$, yield 85.5%. M.p. 145°-147° C.

Elementary analysis (for $C_{51}H_{67}N_9O_{12}S_2$)

|  | C | H | N |
|---|---|---|---|
| Calcd. (%): | 57.67, | 6.36, | 11.87 |
| Found (%): | 57.43, | 6.17, | 11.61 |

(7) Synthesis of Suc—Tyr—Met—Gly—Trp—Met—Asp—MePhe—NH$_2$

A 0.89 g quantity (0.84 mmole) of Boc—Tyr—Met—Gly—Trp—Met—Asp—MePhe—NH$_2$ obtained by the procedure (6) was dissolved in 3 ml of trifluoroacetic acid in the presence of 0.2 ml of ethanedithiol and 0.4 ml of anisole and allowed to stand at room temperature for 30 minutes. Subsequently 100 ml of anhydrous ether was added to the solution, and the solid separating out was filtered off and dried. The product was dissolved in 20 ml of DMF containing 0.12 ml of triethylamine, 0.168 g of succinic anhydride was added to the solution with ice-cooling, and the mixture was stirred at 4° C. for 17 hours. The solvent was thereafter removed in vacuo, and the residue was solidified with 1N citric acid, washed with water and crystallized from methanol-ether, giving 0.68 g of Suc—Tyr—Met—Gly—Trp—Met—Asp—MePhe—NH$_2$, yield 70.8%. M.p. 143°-145° C.

Elementary analysis (for $C_{50}H_{63}N_9O_{13}S_2$)

|  | C | H | N |
|---|---|---|---|
| Calcd. (%): | 56.54, | 5.98, | 11.87 |
| Found (%): | 56.31, | 6.19, | 11.89 |

(8) Synthesis of Suc—Tyr(SO$_3$H)—Met—Gly—Trp—Met—Asp—MePhe—NH$_2$

A 0.57 g portion (0.5 mmole) of the Suc—Tyr—Met—Gly—Trp—Met—Asp—MePhe—NH$_2$ obtained by the procedure (7) was dissolved in 1 ml of pyridine and 13 ml of DMF, and 0.80 g (5.0 mmoles) of pyridine-sulfuric anhydride complex (product of Aldrich Chemical Co., Inc., U.S.A.) was added to the solution with ice-cooling. The mixture was stirred at 0° C. for 30 minutes and then at room temperature for 17 hours. The reaction mixture was concentrated in vacuo, 50 ml of 0.5M aqueous ammonium carbonate solution was added to the concentrate, and the solution was adjusted to a pH of 8.5 with ammonia water. The solution was subjected to DEAE-cellulose column (4 cm×12 cm, product of Brown Co., U.S.A.) chromatography, and the column was washed with 1.5 liters of 0.05M ammonium carbonate-ammonium hydrogencarbonate buffer (pH 8.5) and then eluted with 2 liters of the same buffer (0.3M). UV absorbancy was measured at a wavelength of 278 nm and the fractions containing the desired material were collected. The fraction was concentrated and repeatedly lyophilized to obtain 374 mg of Suc—Tyr($SO_3H$)—Met—Gly—Trp—Met—Asp—MePhe—$NH_2$, yield 65.5%. The peptide obtained will be referred to as "peptide C".

Elementary analysis (for $C_{50}H_{63}N_9O_{16}S_3NH_3 \cdot 4H_2O$)

|  | C | H | N |
|---|---|---|---|
| Calcd. (%): | 48.77, | 5.52, | 11.37 |
| Found (%): | 48.55, | 5.68, | 11.55 |

Result of amino acid analysis by acid decomposition

| Asp 1.02 (1), | Gly 0.99 (1) |
| Met 1.92 (2), | Tyr 1.06 (1) |

Infrared absorption spectrum

A peak peculiar to sulfuric acid ester was found at 1050 $cm^{-1}$.

EXAMPLE 4

Preparation of Suc—Tyr($SO_3H$)—Met—Gly—Trp—Met—Asp—Phe—$NH_2$ (1) Synthesis of Boc—Tyr—Met—Gly—Trp—Met—Asp—Phe—$NH_2$ A 14.16 g quantity (0.016 mole) of Boc—Met—Gly—Trp—Met—Asp—Phe—$NH_2$ [m.p. 195°–197° C., $[\alpha]_D^{24} = -30.0°$ (C=1, DMF); elementary analysis: calcd. for $C_{41}H_{56}N_8O_{10}S_2$ (%) C 55.64, H 6.38, N 12.66, found (%) C 55.85, H 6.55, N 12.54; see M. A. Ondetti et al., Journal of the American Chemical Society, 92, 195 (1970)] was treated at room temperature for 30 minutes with 30 ml of trifluoroacetic acid containing 0.4 ml of ethanedithiol and 0.8 ml of anisole, 300 ml of anhydrous ether was added to the mixture, and the solid separating out was filtered off and dried. The protection-removed hexapeptide obtained was dissolved in 100 ml of DMF, 2.24 ml of triethylamine was added to the solution with ice-cooling, and 12.48 g of Boc-Tyr-Osu was further added thereto. The mixture was stirred overnight at room temperature. The solvent was distilled off in vacuo, and the residue was precipitated with 1N citric acid, collected by filtration, washed with water and crystallized from 100 ml of methanol, giving 11.88 g of Boc—Tyr—Met—Gly—Trp—Met—Asp—Phe—$NH_2$, yield 70.8%. M.p. 183°–187° C.

$[\alpha]_D^{24} = -25.8°$ (C=1, DMF)

Elementary analysis (for $C_{50}H_{65}N_9O_{12}S_2$)

|  | C | H | N |
|---|---|---|---|
| Calcd. (%): | 57.29, | 6.25, | 12.03 |
| Found (%): | 57.09, | 6.38, | 11.96 |

Result of amino acid analysis by acid decomposition

| Asp 1.03 (1), | Gly 0.98 (1), | Met 1.87 (2), |
| Tyr 1.05 (1), | Phe 1.00 (1) | |

Reference: M. Bodanszky et al., Journal of Medicinal Chemistry, 20 (8), 1047 (1977)

(2) Synthesis of Suc—Tyr—Met—Gly—Trp—Met—Asp—Phe—$NH_2$

A 4.193 g portion (4.0 mmoles) of the protected heptapeptide obtained by the procedure (1) was reacted with 0.801 g of succinic anhydride in the same manner as in Example 3, (7), and the resulting product was recrystallized from 50 ml of methanol, giving 2.98 g of Suc—Tyr—Met—Gly—Trp—Met—Asp—Phe—$NH_2$, yield 71.1%. M.p. 196°–197° C.

$[\alpha]_D^{24} = -30.2°$ (C=1, DMF)

Elementary analysis (for $C_{49}H_{61}N_9O_{13}S_2 \cdot H_2O$)

|  | C | H | N |
|---|---|---|---|
| Calcd. (%): | 55.20, | 5.96, | 11.82 |
| Found (%): | 55.19, | 5.99, | 11.63 |

(3) Synthesis of Suc—Tyr($SO_3H$)—Met—Gly—Trp—Met—Asp—Phe—$NH_2$

A 2.10 g portion (2 mmoles) of the Suc—Tyr—Met—Gly—Trp—Met—Asp—Phe—$NH_2$ obtained by the procedure (2) was dissolved in 50 ml of DMF and 5 ml of pyridine, 3.18 g (20 mmoles) of pyridine-sulfuric anhydride complex was added to the solution with ice-cooling, and the mixture was stirred at 0° C. for 30 minutes and then at room temperature for 17 hours. The resulting reaction mixture was purified by DEAE-cellulose column (5×15 cm) chromatography in the same manner as in Example 3, (8). The product was freeze-dried to obtain 1.699 g of Suc—Tyr($SO_3H$)—Met—Gly—Trp—Met—Asp—Phe—$NH_2$, yield 75.3%. This peptide will be referred to as "peptide D".

$[\alpha]_D^{24} = -23.3°$ (C=1, 1N $NH_3$)

Elementary analysis (for $C_{49}H_{61}N_9O_{16}S_3 \cdot NH_3 \cdot 4H_2O$)

|  | C | H | N |
|---|---|---|---|
| Calcd. (%): | 47.68, | 6.12, | 12.48 |
| Found (%): | 47.94, | 5.83, | 12.38 |

Result of amino acid analysis by acid decomposition

| Asp 1.03 (1), | Gly 0.99 (1), | Met 1.98 (2), |
| Tyr 1.00 (1), | Phe 0.99 (1) | |

Infrared absorption spectrum: 1050 $cm^{-1}$

EXAMPLE 5

Preparation of Glt—Tyr(SO₃H)—Met—Gly—Trp—Met—Asp—Phe—NH₂

(1) Synthesis of Glt—Tyr—Met—Gly—Trp—Met—Asp—Phe—NH₂

A 4.193 g portion (4.0 mmoles) of the protected heptapeptide obtained in Example 4, (1) was reacted by the same procedure as in Example 3, (7) with use of 0.913 g of glutaric anhydride. The product was recrystallized from 50 ml of methanol to obtain 3.06 g of Glt—Tyr—Met—Gly—Trp—Met—Asp—Phe—NH₂, yield 72.0%. M.p. 186°–188° C.

$[\alpha]_D^{24} = -26.3°$ (C=1, DMF)

Elementary analysis (for $C_{50}H_{63}N_9O_{13}S_2 \cdot H_2O$)

|  | C | H | N |
|---|---|---|---|
| Calcd. (%): | 55.59, | 6.06, | 11.67 |
| Found (%): | 55.89, | 6.13, | 11.32 |

(2) Synthesis of Glt—Tyr(SO₃H)—Met—Gly—Trp—Met—Asp—Phe—NH₂

A 2.66 g portion (2.5 mmoles) of the Glt—Tyr—Met—Gly—Trp—Met—Asp—Phe—NH₂ obtained above was dissolved in 63 ml of DMF and 6.3 ml of pyridine, 3.98 g (25 mmoles) of pyridine-sulfuric anhydride complex was added to the solution with ice-cooling, and the mixture was stirred at 0° C. for 30 minutes and then at room temperature for 17 hours. The resulting reaction mixture was purified by DEAE-cellulose column (5 cm × 16 cm) chromatography in the same manner as in Example 3, (8), and the product was freeze-dried to give 1.882 g of Glt—Tyr(SO₃H)—Met—Gly—Trp—Met—Asp—Phe—NH₂, yield 65.9%. This peptide will be referred to as "peptide E".

$[\alpha]_D^{24} = -21.6°$ (C=1, 1N NH₃)

Elementary analysis (for $C_{50}H_{63}N_9O_{16}S_3 \cdot NH_3 \cdot 4H_2O$)

|  | C | H | N |
|---|---|---|---|
| Calcd. (%): | 48.77, | 6.06, | 11.37 |
| Found (%): | 48.92, | 5.78, | 11.43 |

Result of amino acid analysis by acid decomposition

| Asp 1.04 (1), | Gly 0.98 (1), | Met 1.99 (2), |
|---|---|---|
| Tyr 1.00 (1), | Phe 1.00 (1) | |

Infrared absorption spectrum: 1050 cm⁻¹

EXAMPLE 6

Preparation of Pht—Tyr(SO₃H)—Met—Gly—Trp—Met—Asp—Phe—NH₂

(1) Synthesis of Pht—Tyr—Met—Gly—Trp—Met—Asp—Phe—NH₂

A 4.193 g portion (4.0 mmoles) of the protected peptide obtained in Example 4, (1) was reacted in the same manner as in Example 3, (7) with use of 1.185 g of phthalic anhydride. The product was recrystallized from 50 ml of methanol, giving 3.14 g of Phe—Tyr—Met—Gly—Trp—Met—Asp—Phe—NH₂, yield 71.6%. M.p. 180°–182° C.

Elementary analysis (for $C_{53}H_{61}N_9O_{13}S_2 \cdot H_2O$)

|  | C | H | N |
|---|---|---|---|
| Calcd. (%): | 57.13, | 5.70, | 11.31 |
| Found (%): | 57.27, | 5.93, | 11.11 |

(2) Synthesis of Pht—Tyr(SO₃H)—Met—Gly—Trp—Met—Asp—Phe—NH₂

A 2.192 g portion (2.0 mmoles) of the Pht—Tyr—Met—Gly—Trp—Met—Asp—Phe—NH₂ obtained above was dissolved in 50 ml of DMF and 5 ml of pyridine, 3.18 g (20 mmoles) of pyridine-sulfuric anhydride complex was added to the solution with ice-cooling, and the mixture was stirred at 0° C. for 30 minutes and then at room temperature for 17 hours. The resulting reaction mixture was purified in the same manner as in Example 3, (8), by DEAE-cellulose column (5 cm × 15 cm) chromatography and freeze-dried to give 1.344 g of Pht—Tyr(SO₃H)—Met—Gly—Trp—Met—Asp—Phe—NH₂, yield 57.1%. This peptide will be referred to as "peptide F".

$[\alpha]_D^{24} = -26.6°$ (C=1, 1N NH₃)

Elementary analysis (for $C_{53}H_{61}N_9O_{16}S_3 \cdot 4H_2O$)

|  | C | H | N |
|---|---|---|---|
| Calcd. (%): | 50.31, | 5.73, | 11.07 |
| Found (%): | 50.48, | 5.36, | 11.15 |

Result of amino acid analysis by acid decomposition

| Asp 1.07 (1), | Gly 1.00 (1), | Met 1.99 (2), |
|---|---|---|
| Tyr 0.99 (1), | Phe 0.99 (1) | |

Infrared absorption spectrum: 1050 cm⁻¹

Peptides C to F were tested for pharmacological effects as stated below.

PHARMACOLOGICAL TEST 5

Effect on the fixed ratio responding in rats

The test was conducted according to the method described in Ahlenius S. and Engel J., Eur. J. Pharm., Vol. 15, 187–192 (1971).

Male Wister rats (weighing 240 to 320 g) were placed into Skinner box (product of Bil-Medika Co., Ltd., Japan, adapted to give a feed when a lever within the box is pressed) and made to learn how to take the food. In this test, one feed was given to the rats when the lever was pressed 20 times, i.e., fixed ratio (FR) 20. The rats showing stable FR20 response were divided into groups each including four rats.

Physiological saline (containing 1 mM of sodium hydrogencarbonate) containing a specified amount of a test compound was subcutaneously given to the rats of one group in a volume of 0.1 ml/100 g. (Physiological saline containing the above-mentioned amount of sodium hydrogencarbonate only was given to the control group). Fifteen minutes after the administration, the test animals were placed in the Skinner box, and the number of times the animals took the feed for 20 minutes was counted. The dose at which the count gained by the group of animals was 50, namely, $ED_{50}$ value, was determined, with the count gained by the control group calculated as 100. The same procedure as above was repeated with use of the other test compounds. Table 4 below shows the results.

TABLE 4

| Test Compound | $ED_{50}$ (μg/kg) |
| --- | --- |
| Peptide C | 2.4 |
| Peptide D | 10.2 |
| Peptide E | 4.0 |
| Peptide F | 16.7 |
| CCK-8 | 22.1 |

Table 4 reveals that the peptides of the present invention inhibit the responding under FR20 schedule in rats at a smaller dose than CCK-8. It is known that this reaction is inhibited specifically by antischizophenic drugs, so that the above results confirm that the present peptides have an antischizophrenic effect.

PHARMACOLOGICAL TEST 6

Inhibitory effect on hyperlocomotion induced by administration of methylphenidate Male ICR mice (weighing 24 to 30 g) were divided into groups, each including 10 mice. To one group of mice were subcutaneously given 10 mg/kg of methylphenidate and 0.1 ml/10 g of a saline solution of a specified amount of a test compound and 1 mM of sodium hydrogencarbonate. One hour after the administration, the test animals were checked for hyperlocomotion, which was measured with use of a device for measuring locomotion of small animals (wherein the motion of an animal shifts the center of graavity of the device to actuate a microswitch for the measurement of the amount of motion, see Folia Pharmacologica Japonica, 74, 629-639 (1978). For a control group, the same procedure as above was repeated except that the saline solution given was free from any test compound. The concentration of the test compound at which the result achieved by the group of animals was 50, namely, $ED_{50}$ value, was determined, with the measurement obtained by the control group calculated as 100. The other compounds were tested in the same manner as above. Table 5 shows the $ED_{50}$ values obtained.

TABLE 5

| Test Compound | $ED_{50}$ (μg/kg) |
| --- | --- |
| Peptide C | 44.7 |
| Peptide D | 34.5 |
| Peptide E | 87.9 |
| Peptide F | 251.3 |
| CCK-8 | 512.5 |

Table 5 reveals that the peptides of the invention all have much higher inhibitory effect on the hyperlocomotion than CCK-8 and that peptide C, D and E exhibit an especially high inhibitory effect.

PHARMACOLOGICAL TEST 7

Effect on climbing behavior induced by apomorphine

Male ddy mice (weighing 20 to 30 g) were used, with 10 mice in each group. Each mouse was placed into a cylindrical cage, 12 cm in diameter and 14 cm in height, made up of vertical rods of 2 mm in diameter spaced apart at a distance of 10 mm in a circular arrangement. The mouse was allowed to stand therein for 2 hours. Physiological saline containing a specified amount of a test compound (and 1 mM of sodium hydrogencarbonate) was subcutaneously given to one group of mice in a volume of 1 ml/10 g. (The same dose of saline only was given to a control group). Ten minutes, 15 minutes, 20 minutes, 25 minutes, 30 minutes, 35 minutes and 40 minutes after the administration of apomorphine, the animal was observed for 1 minutes to obtain 7 scores according to the following criteria and total the seven scores. The test was carried out in soundproof compartments.

0: All the four legs are on the floor.
1: Forelegs are on rods.
2: At least three legs are on rods.

The other compounds were tested in the same manner as above. The test was carried out in soundproof compartments. Student's t-test was resorted to for statistical treatment. Table 6 shows the results.

TABLE 6

| Test compound | Dose (mg/kg) | Average: Mean ± S.E. (total of 7 scores) |
| --- | --- | --- |
| Peptide C | 0.1 | 8.5 ± 1.0 |
|  | 0.3 | 6.6 ± 1.1 |
|  | 1.0 | 5.2 ± 1.0 |
| Peptide D | 0.1 | 7.0 ± 0.3 |
|  | 0.3 | 5.9 ± 0.9 |
|  | 1.0 | 4.5 ± 1.0 |
| Peptide E | 0.1 | 9.1 ± 0.9 |
|  | 0.3 | 7.9 ± 0.9 |
|  | 1.0 | 6.5 ± 0.7 |
| Peptide F | 0.1 | 7.7 ± 0.6 |
|  | 0.3 | 8.0 ± 0.8 |
|  | 1.0 | 6.8 ± 0.8 |
| CCK-8 | 0.01 | 10.2 ± 0.7 |
|  | 0.1 | 11.4 ± 0.6 |
|  | 1.0 | 9.5 ± 1.0 |
| Control | — | 9.8 ± 0.7 |

Table 6 reveals that peptide of the invention significantly inhibit the climbing behavior compared with CCK-8.

We claim:

1. A peptide represented by the formula R—Tyr($SO_3H$)—Met—Gly—Trp—Met—Asp—W—$NH_2$ wherein R is HOOC—A—CO—Asp— (wherein A is lower alkylene), pGlu—Asp—, HOOC—A—CO— (wherein A is lower alkylene) or

and W is Phe or $N^\alpha$-lower alkyl-Phe, or a salt thereof.

2. A peptide as defined in claim 1 which is represented by the formula
R—Tyr($SO_3H$)—Met—Gly—Trp—Met—Asp—Phe—$NH_2$ wherein R is HOOC($CH_2$)$_3$CO—Asp— or pGlu—Asp—, or a salt thereof.

3. A peptide as defined in claim 1 which is represented by the formula
R—Tyr($SO_3H$)—Met—Gly—Trp—Met—Asp—W—$NH_2$ wherein R is HOOC—A—CO— (wherein A is lower alkylene) or

and W is Phe or N$^\alpha$-lower alkyl-Phe, or a salt thereof.

4. A central-nervous-system-suppressing composition for treating patients requiring central-nervous-system-suppression comprising an effective central-nervous-system-suppressing amount of a peptide represented by the formula

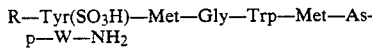

wherein R is HOOC—A—CO—Asp— (wherein A is a lower alkylene), pGlu—Asp—, HOOC—A—CO— (wherein A is lower alkylene) or

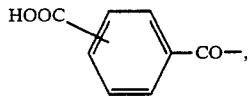

and W is Phe or N$^\alpha$-lower alkyl-Phe, or a salt thereof, and a pharmacologically acceptable, nontoxic carrier.

5. A composition as defined in claim 4 wherein the peptide is represented by the formula

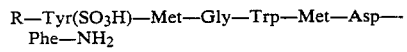

wherein R is HOOC(CH$_2$)$_3$CO—Asp— or pGlu—Asp—, or a salt thereof.

6. A composition as defined in claim 4 wherein the peptide is represented by the formula 7. A peptide as defined in claim 1 which is represented by the formula:

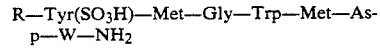

wherein R is HOOC—A—CO—Asp— (wherein A is lower alkylene), pGlu—Asp— or HOOC—A—CO— (wherein A is lower alkylene) and W is Phe or N$^\alpha$-lower alkyl-Phe, or a salt thereof.

8. A peptide as defined in claim 7 which is represented by the formula

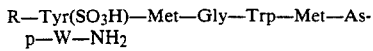

wherein R is HOOC—A—CO— (wherein A is lower alkylene) and W is Phe or N$^\alpha$-lower alkyl-Phe, or a salt thereof.

9. A peptide as defined in claim 8 which is represented by the formula

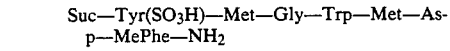

wherein MePhe is N$^\alpha$-methyl-Phe.

10. A peptide as defined in claim 8 which is represented by the formula

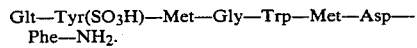

11. A composition as defined in claim 4 wherein the peptide is represented by the formula

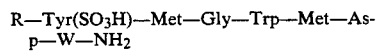

wherein R is HOOC—A—CO—Asp— (wherein A is lower alkylene), pGlu—Asp— or HOOC—A—CO— (wherein A is lower alkylene) and W is Phe or N$^\alpha$-lower alkyl-Phe, or a salt thereof.

12. A composition as defined in claim 11, wherein the peptide is represented by the formula

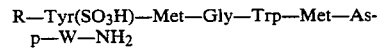

wherein R is HOOC—A—CO— (wherein A is lower alkylene) and W is Phe or N$^\alpha$-lower alkyl-Phe, or a salt thereof.

* * * * *